(12) United States Patent
Kapur

(10) Patent No.: US 11,306,345 B2
(45) Date of Patent: Apr. 19, 2022

(54) INVENTION RELATING TO A MICROBIOLOGICAL TESTING APPARATUS

(71) Applicant: Xcellence in Bio Innovations and Technologies Pvt. Ltd., Hyderabad (IN)

(72) Inventor: Suman Kapur, Hyderabad (IN)

(73) Assignee: Xcellence in Bio Innovations and Technologies Pvt. Ltd.

( * ) Notice: Subject to any disclaimer, the term of this patent is extended or adjusted under 35 U.S.C. 154(b) by 478 days.

(21) Appl. No.: 15/746,424

(22) PCT Filed: Jun. 13, 2016

(86) PCT No.: PCT/IN2016/000153
§ 371 (c)(1),
(2) Date: Jan. 21, 2018

(87) PCT Pub. No.: WO2017/013673
PCT Pub. Date: Jan. 26, 2017

(65) Prior Publication Data
US 2018/0201971 A1  Jul. 19, 2018

(30) Foreign Application Priority Data
Jul. 21, 2015 (IN) .............. 2195-DEL-2015

(51) Int. Cl.
*C12Q 1/18* (2006.01)
*C12Q 1/04* (2006.01)

(52) U.S. Cl.
CPC ....... *C12Q 1/18* (2013.01); *C12Q 1/04* (2013.01)

(58) Field of Classification Search
CPC .................................. C12Q 1/04; C12Q 1/18
See application file for complete search history.

(56) References Cited

U.S. PATENT DOCUMENTS

| | | |
|---|---|---|
| 3,832,532 A | 8/1974 | Praglin et al. |
| 4,236,211 A | 11/1980 | Arvesen |
| 4,591,554 A | 5/1986 | Kaoumura et al. |
| 4,925,789 A | 5/1990 | Edberg |
| 5,064,756 A | 11/1991 | Carr et al. |
| 5,236,827 A | 8/1993 | Sussman et al. |
| 5,457,030 A | 10/1995 | Badal et al. |
| 5,620,865 A | 4/1997 | Chen et al. |
| 5,650,290 A | 7/1997 | Grant |
| 5,922,593 A | 7/1999 | Livingston |
| 6,090,541 A | 7/2000 | Wicks et al. |
| 6,251,624 B1 | 6/2001 | Matsumura et al. |
| 6,387,650 B1 | 5/2002 | Townsend et al. |
| 6,472,167 B1 | 10/2002 | Townsend et al. |
| 6,984,499 B2 | 1/2006 | Chen et al. |
| 7,384,778 B2 | 6/2008 | Chen et al. |
| 2003/0138874 A1* | 7/2003 | Taintor ............ C12Q 1/04 435/34 |

OTHER PUBLICATIONS

Kapur et al., Rapid Sensor Based Technology: A Novel Tool for Direct Antimicrobial Susceptibility Testing in Urinary Tract Infection, Translational Medicine and Biotechnology | vol. 2 | Issue 1 | 2014 http://oiirj.org/oiirj/tmb ISSN 2321-8509—published Aug. 2014.

\* cited by examiner

*Primary Examiner* — Ruth A Davis
(74) *Attorney, Agent, or Firm* — Rattan Nath

(57) ABSTRACT

The abstract particularly describes the nature of this invention and the manner in which it is to be performed:—
1. Specific process and apparatus developed
   The inventor has prepared a novel process to speedily and accurately detect pathogens present in a fluid sample, identify the pathogens and it's count and determine the level of their susceptibility levels to multiple antimicrobial agents and portability of the apparatus for speedy determination of antibiotic susceptibility levels of pre-separated pathogens from a biological sample cultured in a multi-well strip, in any field location
2. Disadvantage and shortcomings in earlier method and benefit of this invention
   It provides result in a ready to use format in four hours time from the start of the assay as against the waiting period of 48 to 72 hours for a sample cultured and tested in a lab using the conventional clinical microbiology.

2 Claims, No Drawings

INVENTION RELATING TO A MICROBIOLOGICAL TESTING APPARATUS

1. TECHNICAL FIELD OF INVENTION

The present invention relates to system and methods for separation, identification, classification and processing of Microbiological Pathogens in a Biological sample. One such method comprises of a ready to use kit for separation of Microbiological pathogens from the biological or clinical sample. Another method includes processing of separated Microbiological Pathogens and a software supported semi-automatic apparatus for identification, classification, determining bacterial load and reporting the antibiotic sensitivity/resistance of the bacteria present in the biological sample.

2. BACKGROUND

Urinary tract infections (UTIs) are commonly known human diseases. UTIs-pose a serious health problem affecting millions of people each year with the total cost of treating such diseases being significantly high. It is estimated that annually approximately 150 million people are diagnosed with UTI's, worldwide. UTI alone is estimated to account for over 10 million-patient visits to doctors per year, having a cost burden of more than a $1 billion. In developing countries, for example India, annually diagnosed cases of UTIs are substantially higher and people per day suffering from UTI are estimated to be around 1 million. Further, irrational use of antibiotics, and the resultant emergence of superbugs, has led to an alarming increase in Anti-Microbial Resistant (AMR). Not only is AMR responsible for longer lasting infections and higher risk of death, it also reduces the effectiveness of the available treatment. Moreover, resistant infections require more advanced and costlier therapies, which results in increased health care costs and financial burden on patients, their families and society as a whole.

The primary causative agents of UTIs are enteric gram negative bacilli that normally reside in the intestinal tract and become pathogenic when found in the urinary tract. Some examples of enteric gram negative bacilli are *Escherichia coli, Klebsiella pneumoniae, Enterobacter, Proteus mirabilis*, etc. Besides the above *Pseudomonas aeruginosa* and some gram positive cocci, such as *Staphylococcus aureus* and *Enterococcus faecalis* could also be termed as urinary pathogens contributing to urinary tract infections.

Medical practitioners at hospitals, clinics, labs and healthcare centres typically recommend bacteriological testing on patients experiencing symptoms of urinary tract infections. Common symptoms of the urinary tract infections are fever, burning sensation, frequent urge to urinate, cloudy urine, etc. For bacteriological testing biological samples such as urine etc. of the patients are collected and subjected to clinical tests. As a process of the test, microorganisms are isolated from the biological samples such as urine etc. and further tested for identification of the pathogens causing urinary tract infection. This entire process of identification and characterization generally requires several tests, and may even include repetition of some tests. The method of identifying the urinary tract infection causing pathogens and determining an appropriate antibiotic treatment regime is however carried out through several known microbial testing means. In one such known testing means, generally referred to as Urine Culture and Sensitivity test, the suspected pathogens are isolated by inoculating the specimen onto a culture medium, which is then incubated at 37° C. for 24-48 hours to ensure bacterial growth. Upon identifying growth, tests for determining antibiotic susceptibility level (susceptible, moderately susceptible or resistant) for the identified pathogens to a set of antimicrobial agents are carried out. The test results obtained are then used by the medical practitioner for prescribing an appropriate antibiotic treatment regimen for treating disease-causing bacteria of UTI.

Antimicrobial susceptibility of the identified bacteria is generally determined by known conventional agar diffusion assay method, or Kirby-Bauer disk-diffusion method. As understood the agar diffusion test involves measuring the effect of an antimicrobial agent against suspected pathogens grown in culture or on agar medium that has been inoculated with the suspect pathogens. In this method the suspected pathogens are spread uniformly across a culture plate. Thereafter, a filter-paper disk, impregnated with the antibiotic compound to be tested, is placed on the surface of the agar. The antibiotic compound diffuses from the filter paper into the agar. The concentration of the antibiotic compound will be highest next to the disk, and will decrease as the distance from the disk increases. In case the antibiotic compound is effective against the suspect pathogen at a particular concentration, no colonies will grow where the concentration in the agar is greater than or equal to the effective concentration. This is the zone of inhibition. Thus, the size of the zone of inhibition is a measure of the antibiotic compound's effectiveness—the larger the clear area around the filter disk, the more effective is the antibiotic compound.

The above known means and methods however have several drawbacks and it is desirable to address them immediately for arresting the impending widespread menace of antimicrobial resistance. First, the commonly used procedures to obtain the information relating to the identified pathogens and antibiotic susceptibility data generally takes 48-72 hours, which considering the nature of the cases is often time-consuming. Due to time delays and cumbersome assay procedures required by conventional culture methods, the practitioners often do not wait for the bacteriological findings to be made available and prescribe wide spectrum antibiotics. However, when the bacteriological findings are received the practitioners may actually be forced to change the treatment regimen. All this leads to irrational use of antibiotics contributing to the emergence of Anti-Microbial Resistance (AMR) in bacteria, and poses a challenge for quality healthcare services. Further, some patients who may be allergic to some type of antibiotics may develop severe allergies due to incorrect prescription of antibiotics.

Second, in developing countries such as India where about 70% of India's 1.2 billion live in remote areas, having little or no access to hospitals, healthcare facilities, clinics and diagnostic labs, and where experienced practitioners, skilled personnel, automatic equipment, etc., are readily not available. Moreover, in the absence of skilled personnel and infrastructure this test is i) not easy to conduct, ii) time consuming and iii) prohibitively expensive if currently available imported machines are deployed. Despite best efforts of the government, healthcare facilities at these places often remain understaffed and lacking in basic equipment and medication. Thus, rather than relying on experienced practitioners many rural patients turn to local pharmacists and take whatever drugs they have in stock. Such a situation further contributes to emerging antibiotic resistance in bacteria.

Third, despite attempts to devise a microbial testing apparatus, which are quite expensive, and related processes for reducing the time consumed in generating the antibiotic susceptibility data and thereby prescribing correct antibiotics, the test-time has not been significantly reduced. All factors put together the practice of empirically prescribing medicines and disregarding the need for culture and sensitivity test prior to prescription of antimicrobial agents has continued and eventually continues to lead to AMR.

Therefore, there is an urgent need for having an improved rapid point of care microbiological testing apparatus and/or assay and its associated methods that substantially reduces the time in conducting the tests and provides automated results. This urgent need when addressed would greatly help in selecting, or even confirming, a proper treatment regimen for UTIs with quick turnaround time and help preventing emergence of antibiotic resistant bacteria. Further, there is also a need to devise an automatic/semiautomatic susceptibility testing apparatus that is easily operable, cost effective, does not require highly skilled personnel, and is devoid of complex testing procedures for performing the antibiotic susceptibility test. Providing such testing devices in large scale volumes would invariably reduce the need of having skilled persons and costly equipment in remote village areas, help in providing better patient care besides containing the spread of antibiotic resistant bacteria, and thereby treating UTIs rapidly and effectively.

3. SUMMARY OF INVENTION

The main object of the present invention is to make available a process to speedily and accurately detect pathogens present in a fluid sample, identify the pathogens and the bacterial load in terms of count and determine the level of their susceptibility to multiple antimicrobial agents.

Second object of the present invention is portability of the apparatus for determination of antibiotic susceptibility of pre-separated pathogens from a biological sample cultured in a multi-well strip, in any field location including primary health care centers, diagnostic testing lab, doctor's clinic, hospital ward, etc.

Accordingly disclosed herein is an aspect of the present invention including a specialized software programme embedded/implanted on a microprocessor which is part of the portable apparatus for rapid identification of the pre-separated pathogens in a fluid sample cultured inside a multi-well strip; except a reference well of the multi-well strip each of the well is preloaded with a distinct antimicrobial agent, the portable apparatus including, an enclosure refined by a top, bottom and four side surfaces. The specialized software programme along with the logical Algorithm which also forms the part of this invention enables microprocessor to sense growth attributes of the pre-separated pathogens from the electrical signals generated by an optical sensor, when the multi-well strip is positioned inside the enclosure, and a microprocessor electrically connected to the sensing mechanism for receiving the corresponding electrical signals; the microprocessor programmed for determining the susceptibility levels of the pre-separated pathogens on the basis of the corresponding electrical signals, and also to transmit and display the susceptibility level of the pre-detected pathogens displayed on a screen electrically connected to the microprocessor.

According to another embodiment, the sensing mechanism includes, a specialized software programme embedded on a microprocessor which senses the growth attributes of the pre-separated pathogens from the electric signals generated and transmitted to the software programmed microprocessor from the sensing device in the apparatus.

According to another embodiment, the microprocessor is programmed on the basis of a Algorithm which provides a data synchronization method, which includes acquiring data from the strips read by the read-out instrument, update records recorded in various services based on user defined functions to which these data are fed, in which each of the data update records an identifier of a data item having been updated successfully in a corresponding service; the data synchronization center compares the data update records with each other and finds a data item which is recorded only in the data update records of some of the services and is not recorded in the data update records of other services, in which the other services are destination services.

Another embodiment of the present invention provides a data synchronization apparatus, configured to be coupled to a microprocessor which based on a data flow diagram, analyzes and processes the information received from the optical sensor. This processed data is internally further qualified as a diagnostic result, based on a stored data base, and returned back as an identified bacterial species, the number of bacteria of the identified species and calculate the susceptibility level of the pre-separated pathogens grown in a corresponding well that is based on the relationship of reading of a specific well containing a distinct antimicrobial agent and the reading of the reference well of the multi-strip thus returning to the display screen and the printer the range and sensitivity of this bacteria to a given antibiotic in the customized panel of antibiotics. The data processing centre also stores the results of all previous tests done in a given period of time and generate a composite report of the frequency of a given pathogen and it's susceptibility profile.

Another aspect of the present invention, is a ready to use kit for detecting pathogens present in a fluid sample including, at least one container that is used for collecting the fluid sample, at least one vial containing culture growth media, at least three or more multi-well strips, preloaded with a distinct antimicrobial agent in each well, except the reference well, at least one vial containing at least 5 ml of sterile water, at least one needle and specially made syringe along with a filter for harvesting pathogens from the fluid sample.

According to yet another aspect of the present invention, a process for rapidly detecting pathogens present in a Biological sample such as urine and determining its susceptibility to specific antimicrobial agents, preloaded in functionalized test strips, using the process including the steps of processing the fluid sample through a specially designed syringe with filter for obtaining the pathogenic fraction of the sample, aspirating a culture media solution in the dispensing container having an opening through which the pathogen carrying culture media solution is aspirated in the container, and dispensing the aspirated culture media solution in a vial, adding a predetermined volume of the dispensed culture media solution in all specially designed multi-well strip, including the reference well and each well of the multi-well strip, incubating all the loaded multi-well strip at a pre-set-incubation temperature for up to 4 hours, and post incubation, detecting growth of the pathogen.

According to some embodiments of the present invention, the pre-functionalized multi-well strip further includes a plurality of transparent wells, and wherein except one of the well of the multi-well strip each of the remaining wells are functionalized with a distinct antimicrobial agent in a manner that retains the bio-activity of the agent when loaded in the respective well post preloading process.

4. LIST OF PREFERRED AND OPTIONAL FEATURES

Various embodiments of the present invention discuss a specialized software programme and a Logical Algorithm implanted on the microprocessor with data processing abilities as described above, of the semi-automated apparatus, a consumable kit and a method for rapid in-vitro detection of urinary pathogens and susceptibility thereof to antimicrobial agents in a biological sample. Biological sample referred in the various embodiments of the present invention is human urine. However, in alternative embodiments instead of human urine other forms of biological sample like ascetic fluid, tissue scrapings and blood could also be used. Further, the apparatus and the consumable kit could be manufactured and sold as one package. However in other embodiments of the present invention the apparatus and the consumable kit could also be manufactured and sold separately. All such alternatives and modifications are considered to be within the scope of the present invention.

A ready to use consumable kit according to one embodiment of the present invention. The kit when opened includes the following items:

| S No. | Components | Quantity |
|---|---|---|
| 1 | Culture growth media in vial FIG. 102 | 1 |
| 2 | Identification Strip | 1, Pi |
| 3 | Multi-well Strips containing preloaded multiple antimicrobial agents | 2 (1 each for P1, P2 and P3)* |
| 5 | Sterile water | 5 ml |
| 6 | Syringe (10 ml) with Needle | 1 |

*Pi strip is custom designed to run identification of most common UTI pathogens.

The components of the kit could be used at any of the medical facilities, or even at home of a patient, in a sequential manner (described in the kit insert) for bacterial harvesting and rapid culture of pathogens present in the infected Biological Sample. A process for bacterial harvesting and rapid culture of pathogens present within the biological samples according to one embodiment of the present invention. The biological sample is collected in a sterile container. Thereafter, BITGEN (media for culture), which is in the powder form, is rehydrated with the sterile water with the help of the syringe provided in the consumable kit and mixed to prepare a solution. Once the above steps are completed, the filter is attached to the syringe and then processing of the urine takes place by aspirating urine in the syringe. Thereafter, filter is taken off and the filtrate is discarded. Thereafter, BITGEN is taken in the syringe and filter is re-attached to the syringe: Then the BITGEN is dispensed slowly (pushed through) the filter in the BITGEN vial, shaken well and finally closed with the dropper cap. The BITGEN is then left undisturbed for about 5 minutes.

Another embodiment of the present invention in which an antibiotic strip preferably made up of polystyrene and covered from the top with the provided lid. For the purposes of bacterial harvesting and culture of pathogens as well as to identify susceptibility of identified pathogen two or more such antibiotic strips are used.

The strip Pi is functionalized to identify the five most prevalent UTI_causing pathogens namely *Escherichia coli, Staphylococcus aureus, Klebsiella pneumonia, Pseudomonas aeruginosa*, and *Enterococcus* sp.

The strip contains a propriety mix of reagents which when mixed with the BITGEN media result in specific chromogenic endpoints in the presence of specific bacterial species. The aspect parameter values from various well positions in combinations are used to identify the pathogens.

Aspect parameter values from the Pi strip are also used to measure the bacterial load, titres (number) of pathogenic microorganism in the test sample.

These antibiotic strips are subjected to preloading of the antibiotics in accordance with an embodiment of the present invention. Each of the antibiotic strip preferably has about 8 compartments and except the first compartment of each of the two antibiotic strips, all the remaining 14 compartments are preloaded with 14 distinct antibiotics listed down in the table. It is to be noted that the concentration and composition of the below listed antibiotics is chosen as per the established Clinical and Laboratory Standards Institute (CLSI) guidelines.

| Sl. No. | Strip 1 | Strip 2 | Strip 3* |
|---|---|---|---|
| 1 | Amoxicillin | Piperacillin | Amoxicillin |
| 2 | Gentamicin | Cefatoxamine | Gentamicin |
| 3 | Amikacin | Kanamycin | Erythromycin |
| 4 | Cefepime | Cefuroxime | Clindamycin |
| 5 | Ofloxacin | Tobramycin | Cefoxitin |
| 6 | Ciprofloxacin | Levofloxacin | Cefotetan |
| 7 | Ceftriaxone | Ampicillin | Cefazolin |

*for use in samples from pregnant women only.

According to another embodiment of the present invention, instead of two antibiotic strips there could also be an additional antibiotic strip for accommodating additional antibiotics. Such embodiments should be considered to be within the scope of the present invention.

5. CLINICAL TEST 426 samples were tested in a blind folded manner in a hospital setting, out of these 234 were found to be positive both by conventional assay and Rightbiotic assay. 183 were found to be negative by both the tests or assays. 9 samples were found to be having bacterial load less than 1000 bacterial cells indicative of sample collection error. On analysis the results derived from Rightbiotic assay were similar to the results shown by the conventional assays. Where both the assays displayed
  Sensitivity: 96.3%
  Specificity: 100%
  False Negative: 0%
  False Positive: 0.02%

| Conventional Assay | | | |
|---|---|---|---|
| | | Positive | Negative |
| RightBiotic | Positive | 234 (a) | 00 (b) |
| | Negative | 09 (c) | 183 (d) |
| Performance Evaluation | | | |
| Sensitivity: | | 96.3% a/(a + c) | |
| Specificity: | | 100% d/(b + d) | |
| False Negative: | | 0% | |
| False Positive: | | 0.02% | |

6. METHOD OF USE

The process of preloading antibiotics in each of the 14 compartments is noted below in accordance with an embodiment of the present invention. Different antibiotic solutions are dispensed into the polystyrene surface of the compartments using a liquid dispensing apparatus. Antibiotics are then dried under negative pressure at room temperature. Antibiotics are loaded and then dried in a manner so that working concentration does not change on revival thereof.

Further, the different antibiotics are dried in such a manner that the antibiotics remain biologically active in the functionalized strips. Thereafter, the strips are sealed and kept at 4 degrees Celsius for further use. The benefit of preloading antibiotics in such a manner is that very minimal quantity of these antibiotics are required as compared to known quantities generally required with known processes of antibiotic susceptibility tests. Additionally, volumes of all the antibiotics required for testing susceptibility levels is also kept consistent with this technique. Furthermore, despite the fact that the antibiotics are preloaded, the antibiotics are barely visible when observed manually (seen).

The preloaded antibiotic strips in accordance with the above embodiment is then unsealed by removing the lid and four (4) drops each of the BITGEN is then placed in each of the 16 compartments of which 14 have the preloaded antibiotics. The antibiotic strips are then closed with the lid and incubated at room temperature (not below 25° C.) or ideally at 37° C. for about 3-4 hours for culture of the pathogens. In case the urine sample has pathogens it would be reflected in the antibiotic strips, at least in the first (or reference well) compartment of both the antibiotic strips as there is no inhibition of-bacterial growth. The remaining 14 compartments may show varied level of bacterial growth depending on the bacterial susceptibility to those antibiotics. The bacterial growth within the preloaded antibiotic compartment will be represented by a change in colour and turbidity of the medium, BITGEN. The intensity of the colour along with other parameters is a measure of the number of growing cells in the presence and absence of a particular antibiotic.

A semi-automatic apparatus for determining susceptibility of antibiotics to the grown pathogens within the compartments of the antibiotic strips. The apparatus is formed of a top surface, a bottom surface and 4 side surfaces. An automatic antibiotic strip loading slider mechanism is also arranged within the enclosure of the apparatus and that is accessed through an opening provided on one of the surfaces of the apparatus. The slider mechanism includes a teethed rack that when positioned within the apparatus is operatively connected to a stepper motor positioned within the enclosure of the apparatus in a secured manner. The teethed rack also includes a mounting plate that is removable, attached from the teethed rack for holding a strip holder. The teethed rack, the mounting plate and the strip holder are fastened with each other with the help of fastening members to provide a rigid assembly. Each of the antibiotic strips having the harvested pathogens after 4 hours, as noted above, are assembled over on the strip holder.

The antibiotic strip holder is made to pass through the opening within the apparatus in a stepped manner for determining sensitivity of the preloaded antibiotics within each of the antibiotic strips. In a similar manner the second, and if necessary the third antibiotic strip, could also be assembled on the strip holder and made to enter the apparatus for determining sensitivity. An operatively connected electronic sensing and display mechanism is also arranged within the enclosure of the apparatus. The electronic sensing and display mechanism that majorly includes optical sensors, microprocessor and an LCD screen primarily ascertains antibiotic susceptibility of the pathogens in each of the compartments and provide readings on the LCD screen. The LCD screen is provided on the top surface of the apparatus. The LCD screen display readings (susceptibility levels) in the form of sensitive, moderately sensitive or resistant for each of the compartments with a particular antibiotic strip which is inserted within the apparatus. The results can also be printed using on board thermal printer.

In order to receive susceptibility level readings from the antibiotic strips immediately after 4 hours of bacteria harvesting, the apparatus is turned on and the antibiotic strip is placed on the side opening. In a stepped manner the antibiotic strip will start entering inside. The optical sensors that are positioned in proximity to the opening will sense the colour of the first compartment and provide the output to the microprocessor as soon as the first compartment comes above it. The output of the sensor that basically reports the reference reading of the pathogens is analysed by the microprocessor preconfigured with a software. In a similar manner readings of the remaining compartments of the antibiotic strip are sent to the microprocessor that finally reports the reference reading of the pathogens present within the first compartment to the LCD screen.

According to an embodiment of the present invention, the software preconfigured within the microprocessor is programmed on the basis of the below suggested logic of calculating the aspect ratio of frequency outputs from the sensor and not the actual colour in the well obtained from any two compartments and then displaying it. Though number of bacteria in a compartment is proportional to the colour produced, however the colour produced is inversely proportional to the frequency and the sensor provides its output in the form of frequency. The microprocessor calculates the susceptibility level readings on the basis of a proprietary method of microprocessor based calculation.

Based on the preset ratio of any given well with the reference well, the programme calculates whether the given sample is sensitive or resistant to the antibiotic in the well on the basis of frequency recorded as a data point per well.

7. BENEFITS

The apparatus is portable, battery operated and provides results in a ready to use format in four hours time from the start of the assay as against the waiting period of 48 to 72 hours for a sample cultured and tested in a lab using the conventional clinical microbiology assays priced in the market anywhere between Rs.350 to Rs.1200 per sample. The assay under this invention is expected to cost about Rs.400/-per sample in spite of the invention leading to significantly reduced reporting (turn around) time. In case of UTI cultures time benefit is much more important over cost, however, the system which is part of this patent application provides benefit of significantly reduced time at zero cost escalation and at a reasonable price.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

I claim:

1. A kit for detection and separation of microbiological pathogens present in a biological sample comprising:
   at least one container that is used for collecting the biological sample;
   at least one vial containing culture growth media;
   one or more multi-well strips wherein at least one well is pre-loaded with an antibiotic and at least one well is a reference well, wherein the reference well does not contain any antibiotic;
   at least one vial containing sterile water; and a needle,
a syringe;
a cap; and
at least one filter for filtering out bacteria from a clinical or biological sample.

2. The kit of claim 1 further comprising at least one specific chromogenic endpoint to identify and quantify bacteria.

* * * * *